United States Patent [19]

Soto et al.

[11] Patent Number: 5,053,570
[45] Date of Patent: Oct. 1, 1991

[54] FLUID BED PARAFFIN AROMATIZATION

[75] Inventors: Jorge L. Soto, Sewell, N.J.; Sergei Yurchak, Media, Pa.

[73] Assignee: Mobil Oil Corporation, Fairfax, Va.

[21] Appl. No.: 524,247

[22] Filed: May 16, 1990

Related U.S. Application Data

[63] Continuation-in-part of Ser. No. 247,551, Sep. 22, 1988, abandoned.

[51] Int. Cl.$^5$ .................................................. C07C 2/00
[52] U.S. Cl. .................................... 585/417; 585/407; 585/418; 585/911; 585/912
[58] Field of Search ............... 585/407, 415, 417, 322, 585/912, 911; 208/DIG. 1; 423/DIG. 12

[56] References Cited

U.S. PATENT DOCUMENTS

| | | | |
|---|---|---|---|
| 3,756,942 | 9/1973 | Cattanach | 208/137 |
| 3,759,821 | 9/1973 | Brennan et al. | 208/93 |
| 3,760,024 | 9/1973 | Cattanach | 260/673 |
| 3,843,741 | 10/1974 | Yan | 585/407 |
| 3,897,328 | 7/1975 | Mitchell | 208/139 |
| 4,018,711 | 4/1977 | Bertdacini | 208/138 |
| 4,716,656 | 1/1988 | Beisswenget et al. | 124/40 |
| 4,716,856 | 1/1988 | Beisswenger et al. | 122/4 D |
| 4,746,762 | 5/1988 | Auidan et al. | 585/415 |
| 4,751,338 | 6/1988 | Tabak et al. | 585/415 |
| 4,751,339 | 6/1988 | Beech, Jr. et al. | 585/415 |
| 4,761,511 | 8/1988 | Barlow | 585/415 |

OTHER PUBLICATIONS

Alien Property Custodian Ser. No. 292,742, Beck et al., Published Jul. 13, 1943.
A. L. Kohl et al., "Process Upgrades Coke to Gas", Hydrocarbon Processing, Jul., 1983, pp. 97-100.
K. Brooks, "Cutting the Cost of Styrene Production", Chemical Week, 12/18/85, pp. 44-45.
H. C. Short, et al., "New Styrene Process Pares Production Costs", Chemical Engineering, 8/19/85, pp. 30-31.
S. F. Wu et al., 21st ACS et al., Intersoc. Energy Convers. Eng. Conf. Proc., 2, pp. 839-845, San Diego, Aug. 25-29, 1986.
W. Worthy, "Hazardous Waste: Treatment Technology Grows", C&EN, Mar. 8, 1982, pp. 10-16.
N. Y. Chen et al., "M2 Forming-A Process for Aromatization of Light hydrocarbons" Ind. Eng. Chem. Process Des. Dev., 1986, 25, pp. 151-155.

*Primary Examiner*—Anthony McFarlane
*Attorney, Agent, or Firm*—Alexander J. McKillop; Charles J. Speciale; Robert B. Furr, Jr.

[57] ABSTRACT

Yield is improved in a fluid-bed catalytic paraffin aromatization process by tailoring heat transfer to match the endothermic heat load within the fluid bed.

18 Claims, 3 Drawing Sheets

FLUID BED PARAFFIN AROMATIZATION

CROSS-REFERENCE TO RELATED APPLICATIONS

This is a continuation-in-part of U.S. application Ser. No. 247,551, filed Sept. 22, 1988, now abandoned, the entire text of which is incorporated herein by reference.

FIELD OF THE INVENTION

The present invention relates to a process for converting aliphatic hydrocarbons to more valuable products. More particularly, the invention provides a method for improving the yield of aromatics in a fluid bed aliphatics upgrading process.

BACKGROUND OF THE INVENTION

Catalytic paraffin aromatization reactions are strongly endothermic, requiring substantial quantities of heat at relatively high temperature. For example, the aromatization of $C_2$–$C_8$ paraffins over a zeolite catalyst having the structure of ZSM-5 requires heat input of about 278–556 kCal per kilogram of feed (500–1000 BTU per pound) at a reaction temperature of about 510° to about 705° C. (950° to 1300° F.). The problem of transferring heat to the fluid bed catalytic paraffin aromatization process has been an obstacle to its commercial development.

Preheating the feedstock to impart sufficient sensible heat for the endothermic aromatization reaction is unattractive for at least two reasons. First, the quantity of sensible heat which can practically be carried by the feedstock is limited, and is typically insufficient to supply the heat of reaction required for industrially feasible conversion rates. For this reason, the reaction is generally self-quenching when feed preheat is used alone. Second, the feed preheat temperatures required to impart sufficient sensible heat to the paraffinic feedstock typically thermally crack the feedstock to less valuable, and more difficult to aromatize, $C_4$- light aliphatic gases.

Preheating the catalyst to a temperature of around 870° C. (1600° F.) in conjunction with the requisite catalyst circulation rate can also effectively transfer the necessary heat for paraffin aromatization to the reaction zone. However, this entails elevated catalyst temperatures which markedly and undesirably accelerate catalyst deactivation.

Circulating a gas through a heat exchanger positioned in the fluidized bed presents problems as well. The high temperatures required in the aromatization reactor bed tend to limit the temperature differences available between the circulating gas and the reactor bed. Further, the heat transfer coefficient between the inner walls of the heat exchanger tubes and the circulating gas is relatively low. Thus, for a given rate of heat transfer, the comparatively low values for the log mean temperature difference and heat transfer coefficient must be offset by relatively large heat transfer areas.

Because the heat exchanger tubes must be positioned within the fluidized bed reactor, more or larger tubes require a larger reactor to maintain the desired catalyst volume. Given that the reactor as well as the exchanger tubes must be alloyed or otherwise designed to withstand the 510°–705° C. reaction temperatures, an increase in size corresponds to markedly higher material and fabrication costs.

In addition to transferring heat to the aromatization reaction zone, it would be desirable to maximize conversion of paraffins to valuable olefinic and aromatic product components. Thus, a process which achieves both effectively delivers thermal energy to the aromatization reaction zone while tailoring yield to favor more valuable products would be highly desirable.

SUMMARY OF THE INVENTION

In a first method aspect, the present invention provides a method for increasing aromatics yield in a fluid bed catalytic paraffin conversion process comprising the steps of:

(a) maintaining a fluid bed of composite catalyst in a reactor, said composite catalyst comprising a zeolite having a Constraint Index of from about 1 to about 12;

(b) determining the endothermic heat load profile of said reactor as a function of fluid bed height for a selected paraffinic feedstock under predetermined conditions of conversion temperature, average catalyst activity and weight hourly space velocity;

(c) contacting said selected paraffinic feedstock with said composite catalyst in said fluid bed of step (a) under conversion conditions to convert at least a portion of said selected paraffinic feedstock to a product stream containing aromatics; and (d) regulating the rate of heat transfer to said reactor in accordance with the heat load profile determined in step (b) to increase aromatics yield by providing substantially isothermal reaction conditions within said fluid bed.

In a second method aspect, the invention provides a method for increasing aromatics yield in a fluid bed catalytic paraffin conversion process comprising the steps of:

(a) maintaining a fluid bed of composite catalyst within a reactor, said composite catalyst comprising a zeolite having a Constraint Index of from about 1 to about 12;

(b) determining the relative endothermic heat loads of a first upper zone and a second lower zone within said fluid bed for a selected paraffinic feedstock under predetermined conditions of conversion temperature, average catalyst activity and weight hourly space velocity;

(c) charging said paraffin-rich feedstock to said fluid bed of step (a) under aromatization conditions to effect endothermic conversion of at least a portion of said paraffin-rich feedstock to a product stream containing aromatics;

(d) providing a heat transfer fluid at elevated temperature having sufficient sensible heat to supply at least a portion of the energy required for said endothermic conversion of step (c);

(e) providing a first heat exchange conduit positioned within said first upper zone of step (b) and a second heat exchange conduit positioned within said lower zone of step (b); and (f) proportioning the flow of said heat transfer fluid between said first heat exchange conduit and said second heat exchange conduit in accordance with the relative endothermic heat loads determined in step (a) to improve aromatics yield.

DETAILED DESCRIPTION

Figure 1:
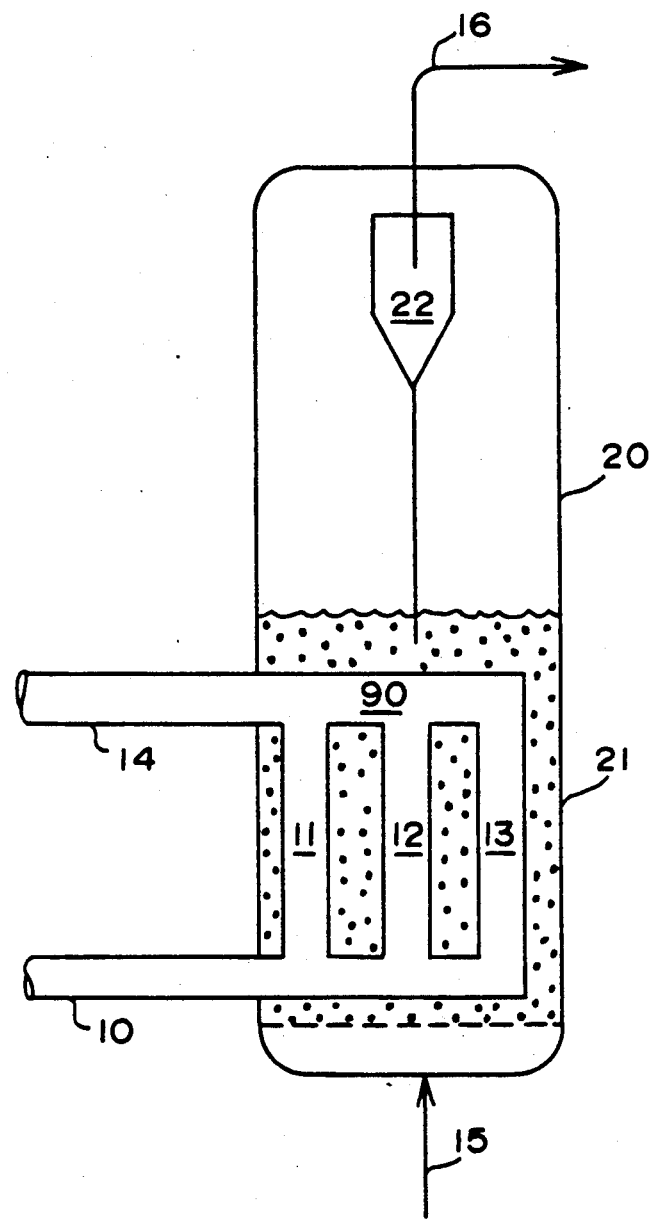
FIG. 1 is a simplified schematic diagram of the reactor of the present invention.

The method and apparatus of the present invention increase heat transfer efficiency to a fluidized bed reaction zone. A method and apparatus are also disclosed for the conversion of aliphatic hydrocarbons to aromatic hydrocarbons.

Conversion Process

Hydrocarbon upgrading reactions compatible with the process of the present invention include high-temperature endothermic conversions of aliphatic hydrocarbons. Depending on the feed composition and process conditions selected, the product stream may comprise light olefins, light olefins and aromatics, or predominately aromatics. For example, a feedstream comprising $C_3-C_5$ aliphatics can produce either a mixture of light olefins and aromatics or mostly aromatics, depending on the catalyst and process conditions with more severe conditions favoring the formation of aromatics. The article "M2-Forming—A Process for Aromatization of Light Hydrocarbons, "by N. Y. Chen and T. Y. Yan, 25 IND. ENG. CHEM. PROCESS DES. DEV. 151 (1986) details the mechanism of such reactions, and is incorporated herein by reference. It is to be understood, however, that the inclusion or a discussion of reaction mechanism is by no means intended to limit the scope of the invention by theory. Process conditions useful in the conversion processes of the present invention are summarized in Table 1.

TABLE 1

| WHSV | Broad range: 0.2–300 hr$^{-1}$ |
| --- | --- |
| | Preferred range: 0.4–5.0 hr$^{-1}$ |
| OPERATING PRESSURE | Broad: 101–2170 kPa (0–300 psig) |
| | Preferred: 170–790 kPa (10–100 psig) |
| OPERATING TEMPERATURE | Broad: 427–820° C. (800–1500° F.) |
| | Preferred: 490–649° C. (850–1200° F.) |

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2-C_4$ paraffins and/or olefins with a crystalline aluminosilicate, e.g. ZSM-5.

U.S. Pat. No. 4,746,762 to Avidan et al. teaches the operation of a fluid bed in the turbulent sub-transport regime. U.S. Pat. No. 4,751,338 to Tabak et al. teaches catalytic aromatization in a fluid bed. Both the Avidan et al. and the Tabak et al. patents are incorporated herein by reference.

Hydrocarbon feedstocks which can be converted according to the present process include various refinery streams including coker gasoline, light FCC gasoline, $C_5-C_7$ fractions of straight run naphthas and pyrolysis gasoline as well as raffinates from a hydrocarbon mixture which has had aromatics removed by a solvent extraction treatment. Examples of such solvent extraction treatments are described on pages 706–709 of the *Kirk-Othmer Encyclopedia of Chemical Technology*, Third Edition, Vol. 9, John Wiley and Sons, 1980. A particular hydrocarbon feedstock derived from such a solvent extraction treatment is a Udex raffinate. The paraffinic hydrocarbon feedstock suitable for use in the present process may comprise at least 75 percent by weight, e.g. 85 percent by weight, of paraffins having from 5 to 10 carbon atoms.

The reaction severity conditions can be controlled to optimize yield of $C_6-C_8$ BTX hydrocarbons. It is understood that aromatics and light olefin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 200 to significantly lower values under steady state operation by controlling catalyst deactivation and regeneration rates to provide an apparent average alpha value (based on total catalyst) below 200, preferably about 10 to 80.

In the fluidized catalyst bed of the present invention the conversion reactions are conducted in a vertical reactor column by passing feedstock gas upwardly through the reaction zone at a velocity greater than dense bed transition velocity and less than transport velocity for the average catalyst particle. In a preferred embodiment, the process is operated continuously by withdrawing a portion of coked catalyst from the reaction zone, oxidatively regenerating the withdrawn catalyst and returning regenerated catalyst to the reaction zone at a rate to control catalyst activity and reaction severity to convert from about 35 to about 95 wt. % of the aromatizable hydrocarbons per pass.

A thermodynamically balanced mixture of exothermic alkenes and endothermic alkanes can be converted without significant recycle and/or diluent. However, a supplemental feedstream or recycle stream such as $C_3$-hydrocarbons can be introduced into the reactor bed. Such a recycle stream can increase $C_5+$ yields while lowering catalyst makeup requirements.

Upgrading of olefins by such hydrogen contributors in fluidized bed cracking and oligomerization units is taught by Owen et al. in U.S. Pat. No. 4,090,949. This technique is particularly useful for operation with a pyrolysis cracking unit to increase overall production of liquid product. In a typical process, the diene-rich $C_4+$ olefinic feedstock is converted in a catalytic reactor under oligomerization conditions and moderate pressure, i.e. 100 to 2500 kPa, to produce a predominantly liquid product consisting essentially of $C_5+$ hydrocarbons rich in gasoline-range mono-olefins and aromatics.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within relatively close tolerances. The highly paraffinic feedstocks most preferred as charge stocks in the present process, however, can upset the temperature profile in even a turbulent fluid bed. One of the advantages of the present process is improved yield which appears to result from substantially isothermal conditions in the fluid-bed reaction zone. Regulating heat flux to the fluid bed in accordance with the endothermic heat load enhances both operating flexibility and temperature stability.

Catalysts

The members of the class of zeolites useful herein for dehydrogenation as well as aromatization reactions have an effective pore size of generally form about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. No. 29,948 (highly siliceous ZSM-5); U.S. Pat. Nos. 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference Zeolite ZSM-23 and the conventional preparation thereof are described in U.S. Pat. No. 4,076,842, the disclosure of which is incorporated herein by referenc . Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. No. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. No. 4,472,535, both of which are incorporated by reference as if set forth at length herein.

Catalysts such as ZSM-5 combined with a Group VIII metal described in U.S. Pat. No. No. 3,856,872, incorporated by reference as if set forth at length herein, are also useful in the present invention.

Catalysts useful herein for dehydrogenation of paraffins comprise a dehydrogenation component and and an inert binder. Dehydrogenation components include metals, preferably including Group VIII metals.

Mixtures of Group VIII metals with other metals on an inert support have also been found to be catalytically active for dehydrogenation. For example, U.S. Pat. No. 4,216,346 to Antos discloses a multimetallic catalyst comprising platinum, cobalt and zinc on an inert porous support. Similarly, U.S. Pat. No. 4,374,046 to Antos teaches a catalyst composition comprising platinum, nickel and zinc on an inert porous support.

Molten-Salt Heat Transfer Media

The molten-salt heat transfer medium as described above transfers heat from a high temperature heat source to a fluidized bed reaction zone. Molten-salt heat transfer media substantially eliminate resistance to heat transfer at the tube wall/heat transfer fluid interface and allow the use of smaller, more economical heat transfer equipment. Molten salts combine two highly desirable characteristics high temperature stability and low resistance to heat transfer. For example, U.S. Pat. No. 4,716,856 teaches a process and apparatus for transferring heat from a circulating fluidized-bed combustion zone in which a salt melt may optionally be used as a heat transfer medium.

Molten salt heat transfer media have also been used in stryene production (Short, H. C. and Botton, L., "New Styrene Process Pares Production Costs", 92 CHEMICAL ENGINEERING 30, (Aug. 19, 1985), and "Cutting the Cost of Styrene Production", 137 CHEMICAL WEEK 44, (Dec. 18, 1985)), as well as in coke gasification (Kohl, A. L. and Ashworth, J. A., "Process Upgrades Coke to Gas", 62 HYDROCARBON PROCESSING 97 (July, 1983)).

For a general discussion of molten salt heat transfer media, see Perry, Robert H. and Chilton, Cecil H., 9 CHEMICAL ENGINEERS HANDBOOK 41, 1973. Examples of suitable salts are shown in Table 2 together with their respective heat capacities. For further data describing suitable salts, see Kelley, K. K., "Contribution to the Data on Theoretical Metallurgy—XIII. High Temperature Heat-Content, Heat-Capacity, and Entropy Data for the Elements and Inorganic Compounds", U.S. Bureau of Mines, Bulletin 584, 1960, and Iwadate, Y., Okada, I., and Kawamura, K. "Density and Heat Capacity of Molten $NaNO_3$-$KNO_3$ Mixtures", 27, J. CHEM. ENG. DATA, 288-290, 1982.

TABLE 2

| Heat Transfer Salt | Heat Capacity (kCal/kg.-°C.) |
|---|---|
| $Na_2CO_3$ | 0.54 |
| $NaNO_3$ | 0.44 |
| $NaNO_2$ | 0.49 |
| $KNO_3$ | 0.28 |

Process Flow

Referring now to FIG. 1, a stream of $C_2$-$C_{10}$ aliphatic hydrocarbons is charged through conduit 15 to a bed of fluidized catalyst 21 in the lower section of reactor vessel 20. The catalyst bed is maintained at a temperature sufficient to vaporize the aliphatic hydrocarbon feed upon its entry into reactor vessel 20. Charge rate is maintained such that the volume of vaporized hydrocarbon will be sufficient to suspend the catalyst in a state of turbulent sub-transport fluidization. The bottom of reactor heat exchanger 90 is spaced above feed distributor grid 28 sufficiently to be free of jet action by feed charged through small diameter holes in the grid. Baffles (not shown) may be added to control radial and axial mixing. Although shown without baffles, the reactor vessel may contain open end tubes above the grid for maintaining hydraulic constraints, as in U.S. Pat. No. 4,251,484 to Daviduk and Haddad.

For a typical feedstream enriched in $C_4$-$C_8$ paraffins, for example a feedstream containing at least about 80% by weight of $C_5$-$C_8$ paraffins, the heat exchanger 90 is preferably located within the bottom 20% of the fluid bed 21, and more preferably in the lower 15% of the fluid bed.

Gaseous reaction products with entrained catalyst enter at least one cyclone separator 22. While only one cyclone is illustrated, it is to be understood that more than one cyclone may be used. Alternatively, one or more cyclones may be used in conjuction with a sintered metal filter positioned outside reactor 20 in conduit 16 to enhance separation of catalyst fines from the reaction products. Reaction products leave reactor 20 through conduit 16.

A stream of molten salt enters reactor heat exchanger 90 through conduit 10. Reactor heat exchanger 90 comprises a plurality of tubes 11, 12 and 13 (only three are shown). The outlet of reactor heat exchanger 90 discharges into conduit 14. The cooled molten salt in conduit 14 is then returned to a high-temperature heat source for reheating.

For fluidized-bed aromatization of aliphatic hydrocarbons, the preferred inlet temperature for the molten salt stream is between about 482° C. and about 982° C. (900° F. and 1800° F.). In general, at least a 38° C. (100° F.) temperature differential between the lower bed temperature and the molten salt inlet temperature should be maintained.

First Embodiment

In a first embodiment of the present invention, the circulating molten salt transfers heat to the fluidized bed reaction zone from a process furnace.

Figure 2:
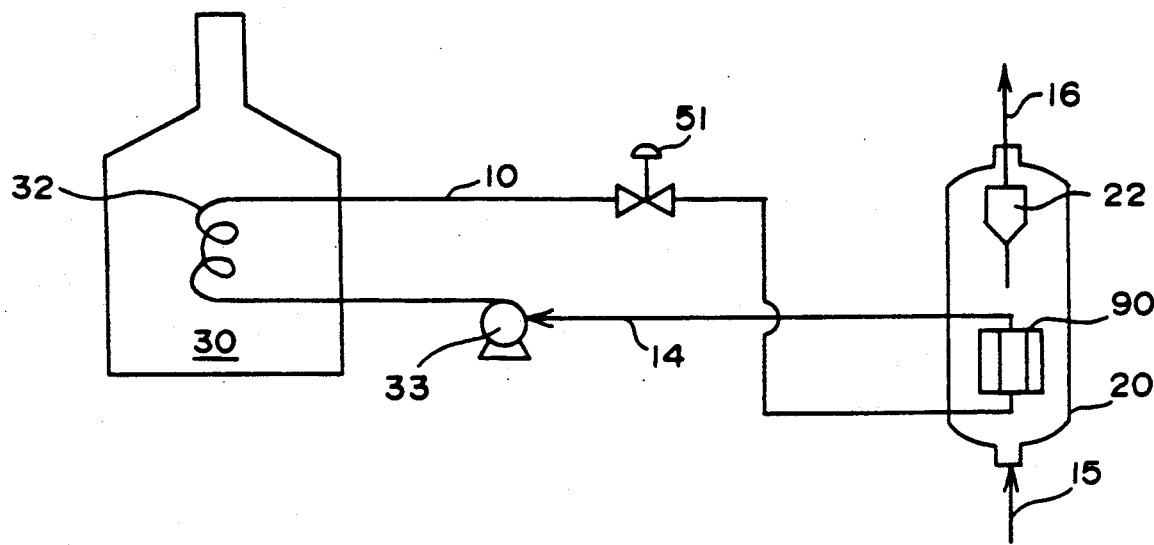
FIG. 2 is a simplified schematic diagram of a first embodiment of the present invention in which a molten-salt heat transfer medium is heated in a process furnace.

Referring to FIG. 2, a stream of hot molten salt enters reactor heat exchanger 90 positioned inside reactor 20 through conduit 10. Flow control valve 51, positioned in conduit 10, contro˙ flow of the hot molten salt to the reactor heat exchanger 90. After flowing through heat exchanger 90, the cooled molten salt is withdrawn via line 14 which is equipped with pump 33 and flows to process furnace 30 where it passes through heater coils 32. The heated mixture leaves process furnace 30 through line 10 and circulates back to heat exchanger 90 as described above.

The heater firing rate and molten salt circulation rate control the quantity of heat transferred to the fluidized catalyst bed. In the present process, the location of heat exchanger 90 correlates with the locus of the endothermic heat load in the reactor, both improving temperature uniformity within the fluid bed and rendering the fluid bed less susceptible to process upsets resulting from variations in feedstock quality.

Maintaining a relatively high $\Delta T$ between the molten salt and the fluidized bed of catalyst enables the present process to achieve the desired heat transfer and therefore the substantially isothermal temperature profile in the fluid bed using a relatively small and economical heat exchanger. The process furnace used in the instant embodiment permits the use of a wide range of molten salt temperatures and flowrates. Generally, the molten salt must be maintained at a temperature above its freezing point for flowability, and at least 38° C. (100° F.) above the fluidized catalyst bed temperature for acceptable heat transfer efficiency. The molten salt maximum temperature is set by the lower of the salt's thermal degradation point or process equipment temperature limitations. The optimum salt temperature and flowrate may be determined with a minimum of trial and error by process control and heat transfer calculations known to those skilled in the art in accordance with the description and examples provided herein.

Second Embodiment

In a second embodiment of the present invention, heat is transferred from an FCC regenerator to the fluidized bed reaction zone. Operating details of FCC units in general and FCC regenerators in particular can be found in: U.S. Pat. Nos. 2,383,636 to Wirth; 2,689,210 to Leffer; 3,338,821 to Moyer et al; 3,812,029 to Snyder, Jr.; 4,093,537 to Gross et al; 4,118,338 to Gross et al and 4,218,306 to Gross et al., as well as in Venuto et al. *Fluid Catalytic Cracking with Zeolite Catalysts*, Marcel Dekker, Inc., (1979). The entire contents of all the above patents and publications are incorporated herein by reference.

Figure 3:
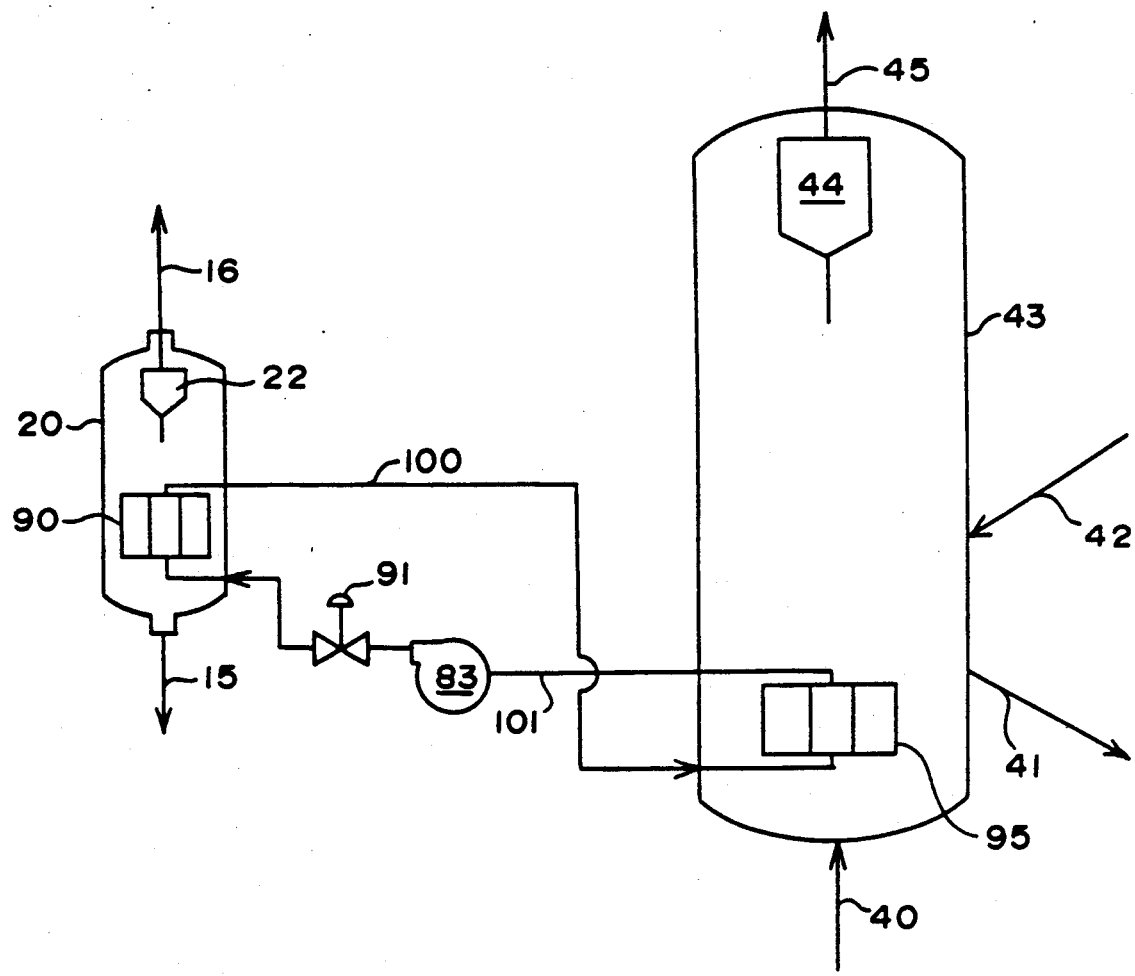
FIG. 3 is a simplified schematic diagram of a second embodiment of the present invention in which a molten-salt heat transfer medium is heated in an FCC unit regenerator.

Referring to FIG. 3, deactivated cracking catalyst from an FCC reactor (not shown) flows through line 42 to regenerator vessel 43. Coke deposited on the deactivated catalyst burns in the presence of the oxygen-containing regeneration gas charged to regenerator 43 through line 40 yielding substantially inert flue gas and regenerated cracking catalyst. The regenerated cracking catalyst leaves vessel 43 through line 41 and returns to the FCC reactor riser (not shown). The flue gas together with catalyst fines rises through the regenerator vessel 43 and enters cyclone separator 44 in which flue gas and regenerated catalyst are separated. The flue gas flows out of vessel 43 through line 45 and is sent to a heat recovery unit, e.g. steam generation.

A stream of hot molten salt flows through line 101 which is equipped with pump 83 and flow control valve 91 and enters reactor heat exchanger 90 positioned inside reactor 20. The molten salt flows through reactor heat exchanger 90 and is cooled as thermal energy is transferred &:o the surrounding fluid-bed reaction zone. Line 100 carries the cooled molten salt out of reactor heat exchanger 90 to reheat exchanger 95 positioned in FCC regenerator 43 where the salt is reheated. Reheated salt is then withdrawn from reheat exchanger 95 and charged to reactor heat exchanger 90 as described above.

In the second embodiment, molten salt circulation controls the quantity of heat transferred to the fluidized bed reactor. The FCC regenerator temperature varies with FCC unit operation typically ranging between about 480° and 760° C. (900° and 1400° F.). While a single reheat exchanger 95 is illustrated, a plurality of reheat exchanger tube banks may be employed in parallel with valving to control the molten salt temperature.

EXAMPLE 1

Process Furnace

The first example shows an operation of the present invention in which heat is transferred indirectly from a process furnace to a fluidized bed reaction zone. Process equipment and piping is configured in accordance with the first embodiment, above.

A mixture of $C_4+$ aliphatic hydrocarbons is charged to the inlet of the aromatization reactor at a rate of 4475 B/SD (barrels per stream day). The composition of the aliphatic charge stream is shown below in Table 3.

TABLE 3

|  | wt. % |
|---|---|
| $C_4$ Paraffins | 0.1 |
| $C_5$ Paraffins | 3.9 |
| $C_5$ Olefins + Aromatics | 0.9 |
| $C_6$ Paraffins | 51.4 |
| $C_6$ Olefins + Aromatics | 3.1 |
| $C_7$ Paraffins | 32.3 |
| $C_{7+}$ Olefins + Aromatics | 0.3 |
| $C_{8+}$ Paraffins + Olefins + Naphthenes | 3.8 |
| $C_6$ Aromatics | 4.2 |
|  | 100 |

The fluidized bed reaction zone is maintained at an average temperature of 663° C. (1225° F.) and a pressure of 103 kPa (0.2 psig). As a result, the aliphatic charge stream is vaporized upon its entry into the fluidized bed reaction zone in the lower section of the reactor. Catalyst level in the reactor is selected to maintain a WHSV of about 0.5 hr$^{-1}$.

The net endothermic heat of reaction required for aromatization of the aliphatic feed is supplied to the reaction zone via indirect heat transfer from a process furnace. As described above, a molten salt heat transfer fluid circulates first through the tubes of a process furnace and then through heat exchange tubes positioned inside the reactor. The furnace fires oil, gas or a mixture of the two at a rate sufficient to provide the net heat of reaction to the reactor. The heat exchange tubes positioned inside the reactor are sized such that a 146° C. (262° F.) log mean temperature differential is maintained between the molten heat transfer fluid and the fluidized bed reaction zone.

A heat transfer salt having a heat capacity of 0.54 kcal/kg-°C. (0.54 BTU/lb-°F.) is circulated through the heat transfer system as described above. At the feedstock charge rate of 20,000 kg/hr, approximately $10.2 \times 10^6$ kcal/hr must be transferred to the reaction zone. The feed inlet temperature is 482° C. (900° F.). The salt inlet and outlet temperatures from the reactor heat exchanger are about 871° C. (1600° F.) and 760° C. (1400° F.), requiring a molten salt circulation rate of about $1.70 \times 10^5$ Kg/hr ($3.74 \times 10^5$ lb/hr).

The composition of the resulting product stream is shown below in Table 4.

TABLE 4

| Hydrogen | 2.2 wt % |
|---|---|
| $C_4-$ Aliphatics | 54.1 wt % |
| $C_5+$ Aliphatics | 2.6 wt % |
| $C_5+$ Aromatics | 41.1 wt % |

EXAMPLE 2

FCC Regenerator

Example 2 illustrates an embodiment of the invention in which a reheat exchanger positioned inside an FCC regenerator heats molten salt which is then charged to a reactor heat exchanger as described above.

Charge rate, reaction zone temperature, pressure and WHSV are all identical to the values shown in Example 1. Molten salt is heated to a temperature of 732° C. (1350° F.) at a circulation rate of $3.4 \times 10^5$ kg/hr ($7.5 \times 10^5$ lb/hr) in the reheat exchanger. The hot molten salt enters the heat exchange tubes positioned within the lower 20% of the fluid bed height within an aromatization reactor at a temperature of at least 718° C. (1325° F.). The product mixture evolved is identical to that of Example 1.

EXAMPLE 3

Mechanical Simplicity

In the third example, the mechanical simplicity of the molten salt system is demonstrated.

Charge rate, reaction zone temperature, pressure and WHSV are all identical to the values shown in Example 1. A hot gas, generated in a furnace, is used to supply the heat to the endothermic reaction. The hot gas enters the reactor heating coil at 871° C. (1600° F.), and leaves at 760° C. (1400° F.). The overall heat transfer coefficient in the heating coils is limited by the hot gas to tube wall heat transfer coefficient, and will have a value of about 195.3 kcal/hr-m$^2$-°C. (40.0 BTU/hr-ft$^2$°F.). In order to provide the required heat load, a heat transfer area of 358.2 m$^2$ (3856.7 ft$^2$) is needed. If the heating coils are made of 9.1 m (30.0 ft) long, 0.05 m (2.0 in)-schedule 40 pipe, 207 tubes are needed to provide the required surface area. When a molten salt is used, the overall heat transfer coefficient is limited by the tube wall to catalyst bed heat transfer coefficient and the overall heat transfer coefficient is much higher, with a value of about 888.6 kcal/hr-m$^2$-°C. (182 BTU/hr-ft$^2$°F.). A surface area of only 78.7 m$^2$ (847.1 ft$^2$), or only 46 tubes, is needed. The much lower number of tubes for the molten salt system allows a smaller diameter reactor and simplifies its mechanical design.

EXAMPLE 4

Example 4 illustrates a method for locating a heat exchange conduit within a fluid-bed aromatization zone in accordance with the present invention.

TABLE 5

| Fluid-Bed Aromatization Zone | |
|---|---|
| Height of Reactor Vessel: | 6.1 m (20 ft.) |
| Height of Fluid Bed: | 4.0 m (16 ft.) |
| Diameter of Fluid Bed: | 1.2 m (4 ft.) |
| Fluid Bed Density: | 400 kg/m$^3$ (25 lb/ft$^3$) |
| Operating Pressure: | 410 kPa (45 psig) |

TABLE 5-continued

| Fluid-Bed Aromatization Zone | |
|---|---|
| Desired Operating Temperature: | 621° C. (1150° F.) |
| Weight Hourly Space Velocity: | 0.5 hr$^{-1}$ |
| Catalyst: | ZSM-5 in an inert binder |

A fluid-bed aromatization reactor is operated in accordance with the conditions set forth in Table 5 using a paraffinic feedstock as described above in Table 3. Thermal energy for the endothermic conversion is derived from feed preheat. Yield loss is noted due to partial thermal cracking of the feedstock. The temperature profile over the fluid bed height, measured by regularly spaced thermocouples, shows a precipitous drop near the fresh feed inlet at the bottom of the fluid bed. Temperature in the lower 20% of the bed height is found to fall below about 427° (800° F.), thus rendering the reaction self-quenching near the fresh feed inlet. From this temperature profile study, the optimum location for the heat exchange conduit is determined to be within the lower 20% of the fluid bed height, more preferably within the lower 15% of the fluid bed height, and most preferably as close to the fresh feed inlet (or fresh feed distributor grid) as possible without disturbing the flow of reactants into the fluid bed.

EXAMPLES 5 and 6

Examples 5 and 6 show the beneficial improvement in valuable aromatics and olefins yield attendant to the improved fluid-bed temperature uniformity of the present invention.

A feedstock enriched in $C_6$–$C_7$ paraffins is charged to the bottom of a fluid bed of ZSM-5 composite catalyst at weight hourly space velocity of 0.5 hr$^{-1}$. Pressure within the reaction zone is controlled at approximately 14.7 psia. Feed conversion of about 40% is attained. The product yield distribution is shown to be dependent upon temperature uniformity within the reaction zone, with more uniform temperature profiles yielding higher concentrations of valuable olefins and aromatics. Results are shown below in Table 6.

TABLE 6

| Reactor Temperature, | | |
|---|---|---|
| Bottom | 567° C. (1052° F.) | 613° C. (1136° F.) |
| Top | 621° C. (1150° F.) | 624° C. (1155° F.) |
| Product Yields, wt. % | | |
| $H_2$ | 1.5 | 1.6 |
| $C_1$ | 8.1 | 8.0 |
| $C_2$ | 7.4 | 6.5 |
| $C_2=$ | 10.0 | 12.5 |
| $C_3$ | 11.2 | 8.2 |
| $C_4=$ | 7.2 | 13.5 |
| Benzene | 6.6 | 8.7 |
| Toluene | 10.7 | 11.4 |
| Valuable Products | | |
| BTX | 22.1 | 25.5 (+3.4) |
| $C_2$–$C_4$ Olefins | 30.2 | 32.4 (+2.2) |

Changes and modifications in the specifically described embodiments can be carried out without departing from the scope of the invention which is intended to be limited only by the scope of the appended claims.

What is claimed is:

1. A method for increasing aromatics yield in a fluid bed catalytic paraffin conversion process comprising the steps of:
   (a) maintaining a fluid bed of catalyst in a reactor, said catalyst comprising a zeolite having a Constraint Index of from about 1 to about 12;
   (b) determining the endothermic heat load profile of said reactor as a function of fluid bed height for a paraffinic feedstock containing at least 50% by weight of $C_3$–$C_8$ paraffins under conditions of conversion temperature, average catalyst activity and weight hourly space velocity sufficient to convert said paraffinic feedstock to a product mixture containing at least 20% by weight of $C_5+$ aromatics;
   (c) contacting said selected paraffinic feedstock with said catalyst in said fluid bed of step (a) under conversion conditions to convert at least a portion of said selected paraffinic feedstock to product stream containing at least 20% by weight of $C_5+$ aromatics; and
   (d) regulating the rate of heat transfer to said reactor and the location of heat transfer within said reactor in accordance with the heat load profile determined as a function of fluid bed height in step (b) to increase aromatics yield by providing substantially isothermal reaction conditions within said fluid bed.

2. The process of claim 1 wherein said regulating step (d) further comprises providing at least two heat exchange conduits positioned within said fluid bed and splitting the flow of a heat transfer fluid between said heat exchange conduits in accordance with the heat load profile determined in step (b).

3. The process of claim 2 wherein said heat transfer fluid comprises a molten salt.

4. The process of claim 1 wherein said fluid bed of step (a) is maintained in a sub-transport flow regime.

5. The process of claim 4 wherein said sub-transport flow regime further comprises a turbulent sub-transport flow regime.

6. The process of claim 1 wherein said conversion conditions comprise weight hourly space velocity from about 0.2 to about 300 hr$^{-1}$, pressure from about 0 to about 300 psig, and temperature from about 800° to about 1500° F.

7. The process of claim 6 wherein said conversion conditions further comprise weight hourly space velocity from about 0.4 to about 5.0 hr$^{-1}$, pressure from about 10 to about 100 psig, and temperature from about 850° to about 1200° F.

8. The process of claim 1 wherein said zeolite has the structure of at least one selected from the group consisting of ZSM-5, ZSM-11, ZSM-12, ZSM-23, ZSM-35, and ZSM-48.

9. The process of claim 8 wherein said zeolite contains gallium or indium.

10. The process of claim 8 wherein said zeolite contains gallium or indium.

11. A method for increasing aromatics yield in a fluid bed catalytic paraffin conversion process comprising the steps of:
   (a) maintaining a fluid bed of catalyst within a reactor, said catalyst comprising a zeolite having a Constraint Index of from about 1 to about 12;
   (b) determining the relative endothermic heat loads of a first upper zone and a second lower zone within said fluid bed for a paraffinic feedstock containing at least 50% by weight of $C_3$–$C_8$ paraffins under predetermined conditions of conversion temperature, average catalyst activity and weight hourly space velocity;

(c) charging said paraffin-rich feedstock to said fluid bed of step (a) under aromatization conditions to effect endothermic conversion of at least a portion of said paraffinic feedstock to a product stream containing at least 20% by weight of $C_{5+}$ aromatics;

(d) providing a heat transfer fluid at elevated temperature having sufficient sensible heat to supply at least a portion of the energy required for said endothermic conversion of step (c);

(e) providing a first heat exchange conduit positioned within said first upper zone of step (b) and a second heat exchange conduit positioned within said lower zone of step (b); and (f) proportioning the flow of said heat transfer fluid between said first heat exchange conduit and said second heat exchange conduit in accordance with the relative endothermic heat loads determined in step (b) to improve aromatics yield.

12. The process of claim 11 wherein said heat transfer fluid comprises a molten salt.

13. The process of claim 11 wherein fluid bed of step (a) is maintained in a sub-transport flow regime.

14. The process of claim 13 wherein said sub-transport flow regime further comprises a turbulent sub-transport flow regime.

15. The process of claim 11 wherein said conversion conditions comprise weight hourly space velocity from about 0.2 to about 300 $hr^{-1}$, pressure from about 0 to about 300 psig, and temperature from about 800° to about 1500° F.

16. The process of claim 12 wherein said conversion conditions further comprise weight hourly space velocity from about 0.4 to about 5.0 $hr^{-1}$, pressure from about 10 to about 100 psig, and temperature from about 850° to about 1200° F.

17. The process of claim 11 wherein said zeolite has the structure of at least one selected from the group consisting of ZSM-5, ZSM-11, ZSM-12, ZSM-23, ZSM-35, and ZSM-48.

18. A method for increasing aromatics yield in a fluid bed catalytic paraffin aromatizaton process comprising the steps of:

(a) maintaining a turbulent fluid bed of finely divided catalyst within a reactor having feed inlet distributor in a lower portion thereof, said catalyst comprising a zeolite having a Constraint Index of from about 1 to about 12;

(b) determining the heat load profile of said reactor as a function of fluid bed height for conversion of a paraffinic feedstock containing at least 50% by weight of $C_3$-$C_8$ paraffins under conditions of conversion temperature, average catalyst activity and weight hourly space velocity sufficient to convert said paraffinic feedstock to a product mixture containing at least 20% by weight of $C_{5+}$ aromatics;

(c) locating an upper boundary from said heat load profile of step (b), said upper boundary defined by the fluid hed height at which said conversion of said paraffinic feedstock is self-quenching; and (d) positioning heat exchange conduit within said fluid bed to increase aromatics yield by providing substantially isothermal reaction conditions within said fluid bed while remaining essentially free of jet action impingement from said paraffinic feedstock enter said reactor through said feed inlet distributor.

* * * * *

UNITED STATES PATENT AND TRADEMARK OFFICE
CERTIFICATE OF CORRECTION

PATENT NO. : 5,053,570

DATED : October 1, 1991

INVENTOR(S) : Soto et al.

It is certified that error appears in the above-identified patent and that said Letters Patent is hereby corrected as shown below:

Column No. 14, Line No. 25 "hed" should be --bed--.

Signed and Sealed this

Eighth Day of June, 1993

Attest:

MICHAEL K. KIRK

*Attesting Officer*  Acting Commissioner of Patents and Trademarks